US012385913B2

(12) United States Patent
Xu et al.

(10) Patent No.: US 12,385,913 B2
(45) Date of Patent: Aug. 12, 2025

(54) METHODS FOR DETECTING ANTI-DRUG ANTIBODIES (71) Applicant: BRISTOL-MYERS SQUIBB COMPANY, Princeton, NJ (US)

(72) Inventors: Weifeng Xu, West Windsor, NJ (US); Renuka C. Pillutla, Bridgewater, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1077 days.

(21) Appl. No.: 17/265,393

(22) PCT Filed: Aug. 2, 2019

(86) PCT No.: PCT/US2019/044819
§ 371 (c)(1),
(2) Date: Feb. 2, 2021

(87) PCT Pub. No.: WO2020/028764
PCT Pub. Date: Feb. 6, 2020

(65) Prior Publication Data
US 2021/0302421 A1 Sep. 30, 2021

Related U.S. Application Data (60) Provisional application No. 62/714,183, filed on Aug. 3, 2018.

(51) Int. Cl.
*G01N 33/543* (2006.01)
*G01N 33/564* (2006.01)
(52) U.S. Cl.
CPC ..... *G01N 33/564* (2013.01); *G01N 33/54326* (2013.01)
(58) Field of Classification Search
None
See application file for complete search history.

(56) References Cited

U.S. PATENT DOCUMENTS

2015/0268238 A1   9/2015   Inganas et al.

FOREIGN PATENT DOCUMENTS

| CN | 1330153 A      | 1/2002 |
| WO | 2018049424 A1  | 3/2018 |

OTHER PUBLICATIONS

Vos et al., Immunoassay interference caused by heterophilic antibodies interacting with biotin, Clin Chem Lab Med, May 2017, 55 (6), pp. e122-e126. (Year: 2017).*
Wu et al., Single-Domain Antibodies as Therapuetuics against Human Viral Diseases, Frontiers in Immunology, Dec. 2017, vol. 8, Article 1802, pp. 1-13. (Year: 2017).*
Chapman, Andrew, PEGylated antibodies and antibody fragments for improved therapy: a review, Advanced Drug Delivery Reviews, 54, 2002, pp. 531-545. (Year: 2002).*
Weifeng Xu et al., "Bead-extraction and heat-dissociation (BEHD): A novel way to overcome drug and matrix interference in Immunogenicity testing", Journal of Immunological Methods, vol. 462, Nov. 1, 2018, pp. 34-41.
Weifeng Xu et al., "Development and validation of a functional cell-based neutralizing antibody assay for iplimumab", Bioanalysis, vol. 10, No. 16, Aug. 1, 2018, pp. 1273-1287.
Weifeng Xu et al., "Development and characterization of a pre-treatment procedure to eliminate human monoclonal antibody therapeutic drug and matrix interference in cell-based functional neutralizing antibody assays", Journal of Immunological Methods, vol. 416, Jan. 1, 2015, pp. 94-104.
Steindl F et al., : "A simple and robust method for the complete dissociation of HIV-1 p24 and other antigens from immune complexes in serum and plasma samples", Journal of Immunological Methods, Elsevier Science Publishers B.V., Amsterdam, NL, vol. 217, No. 1-2, Aug. 1, 1998, pp. 143-151.
Bian Sumin, et al.: "Validation of a Drug-Resistant Anti-Adalimumab Antibody Assay to Monitor Immunogenecity in the Presence of High Concentrations of Adalimumab", The Apps Journal, Springer US, New York, vol. 19, No. 2, Nov. 21, 2016, pp. 468-474.
Bloem et al., "Systematic comparison of drug-tolerant assays for anti-drug antibodies in a cohort of adalimumab-treated rheumatoid arthritis patients", Journal of Immunological Methods vol. 418, pp. 29-38 (2015).
Franz Steindl, et al., "A simple and robust method for the complete dissociation of HIV-1 p24 and other antigens from immune complexes in serum and plasma samples", Journal of Immunological Methods, 217 (1998) 143-151.
Sumin et al., "Validation of a Drug-Resistant Anti-Adalimumab Antibody Assay to Monitor Immunogenicity in the Presence of High Concentrations of Adalimumab", The AAPS Journal, vol. 19, No. 2, pp. 468-474 (2016).
Xu et al., Bead-extraction and heat-dissociation (BEHD): A novel way to overcome drug and matrix interference in immunogenicity testing, Journal of Immunological Methods vol. 462, pp. 34-41 (2018).
Xu et al., "Development and characterization of a pre-treatment procedure to eliminate human monoclonal antibody therapeutic drug and matrix interference in cell-based functional neutralizing antibody assays", Journal of Immunological Methods, vol. 416, pp. 94-104 (2015).
Xu et al., "Development and validation of a functional cell-based neutralizing antibody assay for ipilimumab", Bioanalysis, vol. 10, pp. 1273-1287 (2018).

* cited by examiner

*Primary Examiner* — Gary Counts
(74) *Attorney, Agent, or Firm* — Z. Angela Guo (57) ABSTRACT

In certain embodiments, the present invention provides a method for detecting an anti-drug antibody (ADA) in a sample, comprising: a) pre-treating the sample at a high temperature to dissociate the ADA: drug immune complex in the sample; b) isolating the ADA from the sample by a matrix; c) retrieving the ADA from the matrix using a buffer; and d) detecting the ADA in a cell-based assay or an in vitro assay.

16 Claims, 5 Drawing Sheets

METHODS FOR DETECTING ANTI-DRUG ANTIBODIES

REFERENCE TO RELATED APPLICATIONS

This application is a national phase application under 35 U.S.C. § 371 of International Application No. PCT/US2019/044819 filed on Aug. 2, 2019, which claims the priority benefit of U.S. Provisional Application 62/714,183, filed Aug. 3, 2018; each of which is incorporated herein by reference in its entirety.

BACKGROUND OF THE INVENTION

Biological therapeutics are foreign antigens and can potentially induce immune response resulting in the formation of anti-drug antibodies (ADA), which in turn may lead to a wide range of side effects. Neutralizing antibodies (NAb) belong to a subset of ADA that can bind to the pharmacological activity regions of therapeutic to inhibit or complete neutralize its clinical efficacy. A cell-based functional NAb assay is preferred to characterize its neutralization activity. However, cell-based NAb assays are often vulnerable to drug interference, as well as interference from numerous serum factors, including but not limited to growth factors and disease-related cytokines. Bead Extraction with Acid Dissociation (BEAD) has been successfully applied to remove circulating drugs and/or other interfering factors from human serum samples, thereby enriching for ADA/NAb. However, the harsh acid used in the extraction procedure can cause irreversible denaturing of NAb and lead to underestimated NAb measurement. Hence, there is a need to develop a novel method for detection of neutralizing anti-drug antibodies.

SUMMARY OF THE INVENTION

In certain embodiments, the present invention provides a method for detecting an anti-drug antibody (ADA) in a sample. Such method comprises: a) pre-treating the sample at a high temperature to dissociate the ADA: drug immune complex in the sample; b) isolating the ADA from the sample by a matrix; c) retrieving the ADA from the matrix using a buffer; and d) detecting the ADA in a cell-based assay or an in vitro assay. Optionally, the high temperature is between 60° C. and 68° C. (for example, about 60° C., about 61° C., about 62° C., about 63° C., about 64° C., about 65° C., about 66° C., about 67° C. or about 68° C.). Optionally, the sample is pre-treated at the high temperature for a period between about 30 minutes and about 2 hours (for example, about 30-60 minutes), such as about 30, 35, 40, 45, 50, 55, 60, 65, 70, 75, 80, 85, 90, 95, 100, 105, 110, 115 or 120 minutes.

In certain specific embodiments, the ADA is sensitive to acid treatment. In certain specific embodiments, the drug has a lower thermal stability than the ADA.

Optionally, the drug is selected from an antibody or fragment thereof, a nucleic acid, a peptide, a polypeptide, a peptidomimetic, a carbohydrate, a lipid, or a small molecule compound. Optionally, the sample is a biological sample selected from body fluids, mucus secretions, saliva, blood, whole blood, plasma, and serum. Optionally, the sample is from a subject which has been treated with the drug.

In certain specific embodiments, the ADA is isolated from the sample by contacting with a biotinylated drug, followed by a streptavidin-coated matrix. Alternatively, the ADA is isolated from the sample by a matrix coupled with the drug. For example, the matrix is a magnetic bead.

In certain specific embodiments, the retrieved ADA is detected in a cell-based assay. For example, such assay comprises: i) adding the retrieved ADA to a cell in the presence of the drug; and ii) detecting the ADA by measuring the reduction of activity of the drug on the cell.

In certain specific embodiments, the retrieved ADA is detected in an in vitro assay. For example, such assay comprises: i) contacting the retrieved ADA with the drug labeled with a detectable label; and ii) detecting the ADA by measuring the detectable label. To illustrate, the detectable label is a label selected from a radioactive isotope, an enzyme, a fluorescent label, a chemiluminescent label, and electrochemiluminescent label, and a substrate for an enzymatic detection reaction.

In certain specific embodiments, the drug is an antibody fragment such as a domain antibody. In certain specific embodiments, the drug is pegylated.

In certain specific embodiments, the drug is lulizumab (i.e., a pegylated anti-CD28 domain antibody). For example, this drug is pre-treated at the high temperature of about 62° C. For example, the ADA is detected in the serum sample.

DETAILED DESCRIPTION OF THE INVENTION

The present invention relates to a novel approach for qualitatively and/or quantitatively detecting ADAs from a sample.

In certain embodiments, the present invention provides a method for detecting an anti-drug antibody (ADA) in a sample. Such method comprises: a) pre-treating the sample at a high temperature to dissociate the ADA: drug immune complex in the sample; b) isolating the ADA from the sample by a matrix; c) retrieving the ADA from the matrix using a buffer; and d) detecting the ADA in a cell-based assay or an in vitro assay. Optionally, the high temperature is between 60° C. and 68° C. (for example, about 60° C., about 61° C., about 62° C., about 63° C., about 64° C., about 65° C., about 66° C., about 67° C. or about 68° C.). Optionally, the sample is pre-treated at the high temperature for a period between about 30 minutes and about 2 hours (for example, about 30-60 minutes), such as about 30, 35, 40, 45, 50, 55, 60, 65, 70, 75, 80, 85, 90, 95, 100, 105, 110, 115 or 120 minutes.

In certain specific embodiments, the ADA is sensitive to acid treatment. In certain specific embodiments, the drug has a lower thermal stability than the ADA. Optionally, the drug is selected from an antibody or fragment thereof, a nucleic acid, a peptide, a polypeptide, a peptidomimetic, a carbohydrate, a lipid, or a small molecule compound. Optionally, the sample is a biological sample selected from body fluids, mucus secretions, saliva, blood, whole blood, plasma, and serum. Optionally, the sample is from a subject which has been treated with the drug.

In certain specific embodiments, the ADA is isolated from the sample by contacting with a biotinylated drug, followed by a streptavidin-coated matrix. Alternatively, the ADA is isolated from the sample by a matrix coupled with the drug. For example, the matrix is a magnetic bead.

In certain specific embodiments, the retrieved ADA is detected in a cell-based assay. For example, such assay comprises: i) adding the retrieved ADA to a cell in the presence of the drug; and ii) detecting the ADA by measuring the reduction of activity of the drug on the cell.

In certain specific embodiments, the retrieved ADA is detected in an in vitro assay. For example, such assay comprises: i) contacting the retrieved ADA with the drug labeled with a detectable label; and ii) detecting the ADA by measuring the detectable label. To illustrate, the detectable label is a label selected from a radioactive isotope, an enzyme, a fluorescent label, a chemiluminescent label, and electrochemiluminescent label, and a substrate for an enzymatic detection reaction.

In certain specific embodiments, the drug is an antibody fragment such as a domain antibody. In certain specific embodiments, the drug is pegylated.

In certain specific embodiments, the drug is lulizumab (i.e., a pegylated anti-CD28 domain antibody; also referred to as BMS-931699). For example, this drug is pre-treated at the high temperature of about 62° C. For example, the ADA is detected in the serum sample.

In order that the present invention may be more readily understood, certain terms are first defined. Additional definitions are set forth throughout the detailed description.

"Anti-drug antibodies" or "ADAs" are antibodies that bind specifically to any region of a drug. For example, an anti-drug antibody may be an antibody or fragment thereof, which may be directed against any region of a drug antibody, e.g., the variable domain, the constant domains, or the glycostructure of the antibody. Such anti-drug antibodies may occur during drug therapy as an immunogenic reaction of a patient. An ADA may be one of any human immunoglobulin isotype (e.g., IgM, IgE, IgA, IgG, IgD) or IgG subclass (IgG1, 2, 3, and 4). ADAs include ADAs from any animal source, including, for example, human or non-human animal (e.g. veterinary) sources.

For the purpose of the present specification, the term "Nab" or "neutralizing antibody" refers to a subset of ADA that can bind to the pharmacological activity regions of a therapeutic drug to inhibit or complete neutralize its clinical efficacy.

In the context of the invention, the term "patient" refers to any subject, preferably a mammal, and more preferably a human, with a disease or suspected of having a disease. The term "subject," as used herein, refers to any animal (e.g., a human or non-human animal subject). In some instances, the subject is a mammal. In some instances, the term "subject", as used herein, refers to a human (e.g., a man, a woman, or a child). In some instances, the term "subject", as used herein, refers to laboratory animal of an animal model study.

As used herein, the term "biological sample" or "sample" refers to a sample obtained or derived from a patient which comprises patient derived immunoglobulin and may therefore be referred to as an immunoglobulin sample. By way of example, a biological sample comprises a material selected from the group consisting of body fluids, blood, whole blood, plasma, serum, mucus secretions, saliva, cerebrospinal fluid (CSF), bronchoalveolar lavage fluid (BALF), fluids of the eye (e.g., vitreous fluid, aqueous humor), lymph fluid, lymph node tissue, spleen tissue, bone marrow, and an immunoglobulin enriched fraction derived from one or more of these tissues. In some embodiments the sample is, or comprises blood serum or is an immunoglobulin enriched fraction derived from blood serum or blood. The sample is, or can be derived (obtained) from, a bodily fluid or body tissue. In some embodiments, the sample is obtained from a subject who has been exposed to the drug, such as repeatedly exposed to the same drug. In other embodiments, the sample is obtained from a subject who has not recently been exposed to the drug, or obtained from the subject prior to the planned administration of the drug.

As used herein, lulizumab is an anti-human CD28 receptor antagonist Vk domain antibody (dAb), formatted with 40 kDa branched polyethylene glycol (PEG), that is being developed for subcutaneous (SC) treatment of autoimmune and inflammatory diseases (e.g., systemic lupus erythematosis). For example, lulizumab has been referenced in U.S. Pat. Nos. 8,168,759, 8,454,959, and 9,085,629.

As used herein, "CD28 activity" is an activity involving or resulting from the binding of CD80, CD86 and/or another ligand to CD28, and includes, but is not limited to, activation of CD28-mediated cell signaling. CD28 activity also includes the induction of T cell proliferation and the induction of cytokine secretion, e.g., interleukin 2 (IL-2), by T cells.

By "domain antibody" is meant a folded polypeptide domain which comprises a sequence characteristic of immunoglobulin variable domains of either the heavy (VH) or light (VL) chains of an antibody and which specifically binds an antigen. A "domain antibody" therefore includes complete antibody variable domains as well as modified variable domains, for example in which one or more loops have been replaced by sequences which are not characteristic of antibody variable domains, or antibody variable domains which have been truncated or comprise N- or C-terminal extensions, as well as folded fragments of variable domains and the target antigen specificity of the full-length domain. A "dAb" is used interchangeably with "domain antibody" herein.

As used herein, an entity (e.g., antibody, anti-drug antibody, drug, protein, enzyme, antibody, antibody fragment, multiple domain biotherapeutics (e.g., antibody drug conjugates), or related species) that is modified by the term "labeled" includes any entity that is conjugated with another molecule or chemical entity a that is empirically detectable (e.g., "detectable label"). Chemical species suitable as labels for labeled-entities include, but are not limited to, enzymes, fluorescent dyes; quantum dots; optical dyes; luminescent dyes; and radionuclides.

The present invention is further illustrated by the following examples which should not be construed as further limiting. The contents of all figures and all references, patents and published patent applications cited throughout this application are expressly incorporated herein by reference.

Example 1

1. Introduction

Biologic therapeutics, or biotherapeutics, have been approved for the treatment of many disease conditions. Despite many advantages over traditional small molecules, biotherapeutics have the potential to induce immune response against themselves, typically referred to as immunogenicity (1). Immunogenicity is a natural defense mechanism of the human body and is usually protective. As part of the adaptive immune response, when a host encounters exogenous proteins or altered self-antigens such as infectious pathogens, tumor antigens or vaccines, the body may develop antibodies against these foreign/altered self-proteins. However, in the case of biotherapeutics, these drug-specific antibodies, commonly called anti-drug antibodies (ADA), can induce a wide range of safety related events ranging from localized infusion reactions to more serious adverse events such as life-threatening hypersensitivities and pure red cell aplasia, PRCA (2, 3). In addition, ADA can lead to reduced drug efficacy (4-6).

The reduced drug efficacy induced by ADA is either due to accelerated drug clearance or a special sub-population of ADA, neutralizing ADA or NAb, which diminish therapeutic efficacy by either preventing the drug from binding to its target or inhibiting downstream signaling upon binding due to steric hindrance. It is currently recommended by health authorities that a functional cell-based NAb assay is implemented whenever possible for the characterization of the neutralizing potential of ADA (7). In a conventional cell-based functional NAb assay, a fixed amount of drug designated as system drug is added to the cells as control; any statistically significant signal change due to the presence of NAb, implies the presence of neutralizing activity in the sample. In the presence of circulating drug from treatment, and depending on the molar ratio of NAb to drug in the sample, NAb may be in complex with drug and no longer available to bind to the system drug in the bioassay; this leads to reduced or false-negative NAb detection. High levels of mAb therapeutics in patient samples are particularly problematic for functional cell-based NAb bioassays (8).

In addition, clinical serum samples may contain matrix components (growth factors, cytokines, etc.) that often directly affect cells and may impact the functional assay readout regardless of NAb presence. While small perturbations from interfering factors in the functional bioassay readout may be tolerable, subject-to-subject and temporal variability may make it impossible to accurately characterize a sample for the presence of NAbs.

A Bead Extraction with Acid Dissociation (BEAD) sample pretreatment procedure has been modified and optimized to treat both drug and matrix interference by using acid to dissociate the drug/ADA immune complex, followed by addition of excess biotinylated drug to compete for ADA binding. Biotinylated drug/ADA complexes are then captured by streptavidin-coated magnetic beads while serum factors and drug are removed by washing (9). Although it has been successfully applied to multiple projects (10), biotherapeutics conjugated with polyethylene glycol (PEG) may not be compatible with this acid dissociation-based extraction, as the case of lulizumab. Lulizumab is an anti-human cluster of differentiation 28 (CD28) receptor antagonist immunoglobulin light chain variable region (VK) domain antibody (dAb) formatted with 40-kilo Dalton (kDa) branched PEG. Alternatively, we took advantage of the lower thermal stability of the domain Ab by heating samples at 62° C. which not only disrupted the drug/ADA immune complex but also selectively denatured the domain Ab drug. As the first step for the disruption of drug/ADA complexes, acid is used in the BEAD method; upon neutralization, excess circulating drug competes with biotin-drug for ADA binding, which requires much higher amounts of biotin-drug to outcompete the drug. The irreversible denaturation of the domain Ab drug at 62° C., thus is superior to the acid-based BEAD method since much less biotin-drug is needed. In addition, using heat instead of harsh acid to eliminate the first step of acid treatment may preserve acid-sensitive NAb species.

2. Material and Methods 2.1. Reagents

RPMI-1640, heat-inactivated fetal bovine serum (FBS), G418, HEPES and sodium pyruvate were purchased from Gibco/Life Technology (Grand Island, NY). The NeoLite Luciferase Reporter Gene Assay System was purchased from PerkinElmer (Waltham, MA), and Hi-Sur Mag Streptavidin Beads were from OceanNanotech (San Diego, CA). Pooled human serum, individual normal human serum, and individual diseased lupus human serum were purchased from Bioreclamation (Hicksville, NY). The Jurkat T cell and Raji B cell lines were originally obtained from ATCC, and the Jurkat T cells were further modified to generate Jurkat. CA cells, which stably express IL-2-driven luciferase. The neutralizing positive control is a proprietary monoclonal mouse affinity-purified antibody to the drug product.

2.2. Cell Culture

The stably transfected Jurkat cells expressing IL-2-driven luciferase (Jurkat.CA) and Raji cells were expanded in vented cap cell culture flasks (BD Falcon, Franklin Lakes, NJ) at 37° C., 5% CO2 and 95% relative humidity (RH). The growth medium was RPMI 1640 with 10% heat-inactivated FBS for both cells. The Jurkat. CA cell line growth medium also contained 400 µg/mL G418, HEPES and sodium pyruvate. The cryomedium for both cell lines was pure FBS supplemented with 10% DMSO. Upon thaw, cells were washed once and resuspended in bioassay medium (RPMI-1640 medium supplemented with 10% FBS) and used directly in the bioassay.

2.3. Preparation of Test Controls for Bead Extraction and Acid Dissociation (BEAD) Procedure Different concentrations of NAb PC were spiked in pooled or individual healthy human serum, with or without 5 µg/ml drug product, and incubated with rotation at room temperature for 4 hours to allow for the formation of immune complexes. Different concentrations of drug product were also spiked into human serum and prepared in the same way. Samples were then aliquoted and frozen at −70 °C until use.

2.4. Bead Extraction and Acid Dissociation (BEAD) and Bead Extraction and Heating Dissociation (BEHD) Procedure We adapted a previously published solid phase or bead extraction with acid dissociation (BEAD) procedure to extract ADA with minor modifications (9). Briefly, 100 μL of human serum samples and control samples prepared above were first mixed with an equal volume of 400 mM glycine-HCl, pH 2.0, and incubated at room temperature (RT) for 60 min on a shaker (Labnet Orbit P4, Woodbridge, NJ) at 1200 rpm. Each sample was then neutralized with 28 μL 1.8 M Trizma Base (pH 8.8) containing 50 μg/mL biotinylated-drug and incubated for 90 min on a shaker at 1200 rpm. Alternatively, 100 μL controls and samples were added to a KingFisher Deep well 96 well polypropylene plate, covered with a plate sealer and incubated for 40-60 min in an Eppendorf Thermomixer R, set at 62° C. and shaking at 400 rpm. After cooling the deep well plate for ~15 minutes, 28 μL of the biotinylated-drug (50 μg/mL diluted in 1% BSA in DPBS) was then added and the sample plate was incubated overnight at 2-8° C. with shaking at 1000 rpm. ADAs, dissociated from drug product and bound to biotin-drug from either the acid or heating treatment, were then immobilized on 250 μg of Streptavidin-coated magnetic beads (25 μL added at 10 mg/mL and incubated for 60 minutes at RT with shaking at 1000-1200 rpm). Bead-complexes were then captured by a magnetic plate, washed twice with 600 μL of PBST and eluted with 60 μL 2×RPMI-1640, pH 2.3 using a KingFisher Flex Magnetic Particle Processor (Thermo Scientific, Waltham, MA). Fifty μL of the final eluted solution was transferred to a new 96 well polypropylene plate containing 22 μL of 100 mM HEPES, pH 8.2.

2.5. Bioassay for Detecting Neutralizing Activity

The IL-2-luciferease bioassay was used to assess the absence, presence, or relative level of the anti-therapeutic protein neutralizing antibodies in the samples. Briefly, 30 μL of neutralized BEAD eluate from section 2.4. was incubated with 15 μL of 250 ng/ml of system drug in a 96 well half area white plate for 20-40 min at RT. Jurkat.CA cells were thawed, washed and resuspended to a final concentration of $3.0 \times 10^6$ cell/mL in bioassay medium (10% FBS in RPMI 1640) and 15 μL was added to the plate and incubated at RT for another 20 min. At the last step, Raji cells were thawed, washed, and resuspended to a final concentration of $1.5 \times 10^6$ cell/mL in bioassay medium containing 2.5 μg/mL anti-human CD3 Ab, 15 μL of this was added to the plate, mixed and then transferred to an incubator set at 37° C., 5% $CO_2$, and 95% humidity for 4 h. After incubation, 75 μL of Neolite Luciferase solution was added to each well, mixed, placed in a dark RT incubator with shaking at 500 rpm, centrifuged and then read using an EnSpire (PerkinElmer, Waltham, MA) plate reader with a default 96-well luminescence protocol.

2.6. DSF for Protein Thermal Stability

Differential scanning fluorimetry with concurrent static light scattering was performed on the UNcle platform (Unchained Labs Inc.). Briefly, purified protein samples were diluted to 1 mg/mL in DPBS buffer, pH 7.2 (Thermofisher) and 9 μL of each was loaded into a microcuvette arrays in triplicate. The extent of sample aggregation was determined by online dynamic light scattering prior to run initiation. Temperature-induced protein unfolding was determined by measuring changes in intrinsic fluorescence by heating from 20° C. to 85° C. using a 1° C. step gradient with a 30 sec temperature stabilization at each step. The Tm (midpoint of the unfolding curve, corresponding to the melting temperature) was calculated in the UNcle Software, using the barycentric fluorescence in nanometers, as a function of temperature in degrees Celsius. Concurrent static light scattering at 266 nm and 473 nm was recorded to detect and control for aggregate formation during the course of the experiment.

2.7 Statistical Methods 2.7.1 Control Precision Assessment

Variance components methods in the context of an analysis of variance (ANOVA) model were used to calculate estimates of precision for the control samples (11). The ANOVA model included factors for analyst, assay day and assay plate within day. Estimates of inter-analyst, inter-day, inter-plate and intra-plate variances were computed in the ANOVA model, and each was expressed as a standard deviation (SD), then as a coefficient of variation (CV [%]=100*SD/mean). The total standard deviation (Total SD) was computed as the square root of the sum of these variance estimates. Total CV (%) (100*Total SD/mean) was used to set plate acceptance.

2.7.2 Cut Point Assessment

Each lupus patient sample was assayed on 6 different occasions, twice by 3 analysts. The NAb assay cut point was calculated using published methods (12). To correct for plate-to-plate fluctuations in RLUs across days, the ratio of patient sample RLU to plate Negative Control (NegC) RLU (average duplicates for each) was computed. Since ratios were used for the cut point assessment, the correlation between patient sample RLU and NegC RLU from the same plate was calculated and the data were plotted. A positive correlation would support use of the ratio method of calculation.

To calculate the NAb assay cut point, the normality of the distribution of sample ratios was assessed. Outliers were evaluated on the basis of the individual ratios for each patient sample. Values were considered outliers if they were below the 25th percentile of the distribution minus 3 times the inter-quartile range, or if they exceeded the 75th percentile of the distribution plus 3 times the inter-quartile range.

After outlier exclusion and log transformation to normality, the NAb assay cut point was calculated as the lower bound on a one-sided parametric 99% interval for the ratios. The form of the equation utilized was:

NAb Assay Cut Point=
$EXP(Mean_{Ratio} - z \cdot TotalSD_{Ratio})$.

In the equation, '$Mean_{Ratio}$' is the mean of the log ratios after outlier exclusion; 'z' is the value for the 'z-score' from the normal distribution corresponding to the lower 1% tail area under the normal curve (2.33); and '$TotalSD_{Ratio}$' is the estimate of the total standard deviation for the log of the ratios after outlier exclusion. 'EXP' is the antilog of the expression.

3. Results 3.1. Therapeutic-Induced Inhibition of IL-2 Production in a Cell Assay Lulizumab is an anti-human CD28 antagonistic immunoglobulin light chain variable region (Vκ) dAb formatted with 40-kDa branched PEG. It is a potent inhibitor of T-cell activation and is a pure antagonist as determined by in vitro agonist, costimulation, and cross-linking experiments (13-

Figure 1:
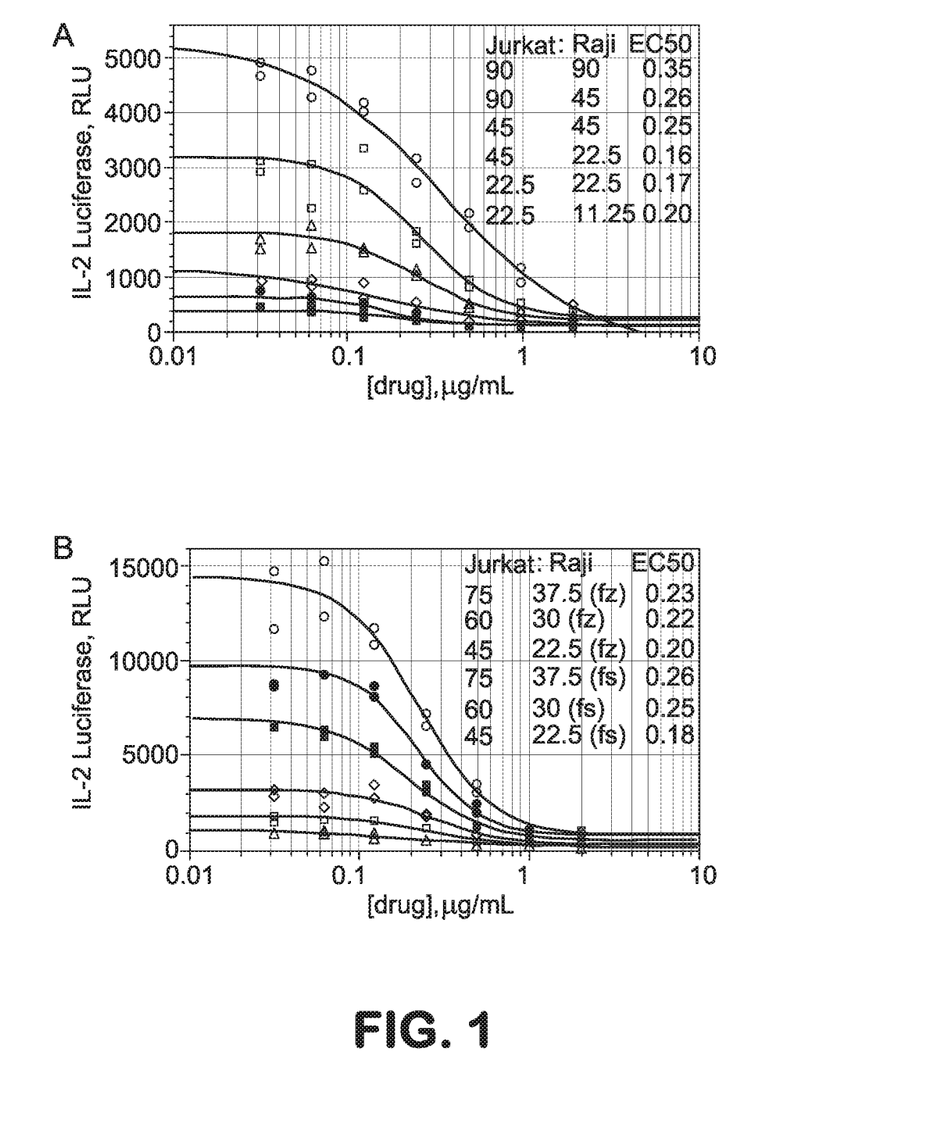
FIG. 1. Lulizumab inhibited T cell activation and IL-2-driven luciferase reporter production in a Jurkat. CA and Raji dual-cell bioassay in a dose-dependent manner with either cells from continuous-culture or freshly-thawed cells. A). Cells from continuous-culture. Different color lines indicate different cell numbers per well (unit: ×103). B). Thawed frozen cells (fz) performed better when compared to fresh cells from continuous-culture (fs). Curves were generated with Softmax from duplicate wells.

15). As shown in FIG. 1A, Jurkat.CA cells from continuous culture produced high levels of IL-2 promoter-driven luciferase reporter when activated by an agonistic anti-CD3 Ab and Raji B cells (which provide CD80/CD86 to engage CD28 on Jurkat.CA cells). Lulizumab inhibited T cell activation and luciferase reporter production in a dose dependent manner (FIG. 1A).

To make downstream sample testing easier, frozen cells were thawed and used in the assay immediately to see whether frozen cells could be used as a ready-to-plate reagent, eliminating the need for the approximate 3-7 day wait time for frozen cells to recover and begin continuous cell culture maintenance. Much higher raw signals were found in the freshly thawed cells when compared to cells from continuous culture (FIG. 1B). Different number and ratio of Jurkat.CA and Raji cells showed different raw signal, response window, as well as sensitivity as indicated by the EC50 of each curve. Forty-five thousand Jurkat. CA cells and 22.5 thousand Raji cells per well were chosen for further assay development and optimization for a balance of raw signal and total cell number needed. (FIG. 1B and Table 1).

TABLE 1

Raw signal of IL-2 luciferase production with different number and ratio of Jurkat and Raji cells

|  |  | Cultured cells | | | Freshly thawed cells | | |
| --- | --- | --- | --- | --- | --- | --- | --- |
| Jurkat cell, x10^3 | | 75 | 60 | 45 | 75 | 60 | 45 |
| Raji cell, x10^3 | | 37.5 | 30 | 22.5 | 37.5 | 30 | 22.5 |
| Drug, μg/mL | 2 | 320 | 260 | 205 | 1015 | 880 | 770 |
| | 1 | 455 | 310 | 180 | 1235 | 825 | 640 |
| | 0.5 | 865 | 480 | 290 | 3185 | 2095 | 1145 |
| | 0.25 | 1710 | 1075 | 530 | 6820 | 4470 | 3180 |
| | 0.125 | 2955 | 1485 | 750 | 11315 | 8315 | 5205 |
| | 0.0625 | 2625 | 1740 | 940 | 13820 | 9220 | 6095 |
| | 0.03125 | 2995 | 1610 | 915 | 13260 | 8660 | 6590 |
| | 0 | 3555 | 2000 | 1215 | 15105 | 10795 | 7305 |
| | S/N | 11.1 | 7.7 | 5.9 | 14.9 | 12.3 | 9.5 |

3.2. Neutralizing Abs Against Lulizumab Rescued IL-2 Production

Figure 2:
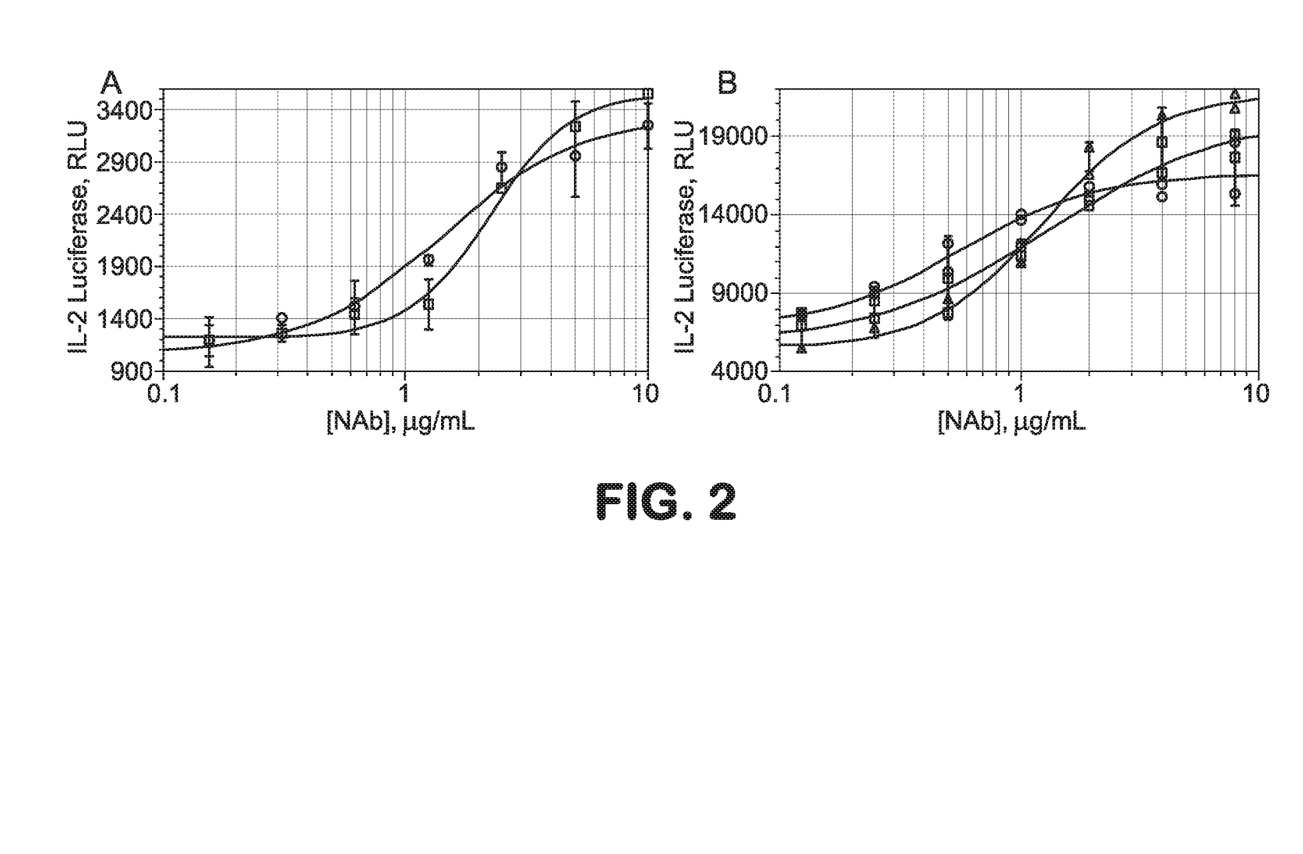
FIG. 2. A). NAb PC rescued IL-2 production inhibited by lulizumab. Red: rabbit polyclonal Abs with EC50 of 2.22; Blue: mouse mAb clone 13H4 with EC50 of 1.45. B). NAb PC curves (mouse mAb clone 13H4) in the presence of different amounts of lulizumab. (Blue, red and green lines represent 0.2, 0.25 and 0.3 µg/mL of lulizumab, with EC50 of 0.53, 0.96 and 1.09, respectively).

A panel of potential NAb positive controls (PCs) were screened in the cell assay, and the most potent clones was chosen. As shown in FIG. 2A, both a rabbit polyclonal Ab (pAb) and mouse monoclonal Ab (mAb) PCs rescued luciferase reporter expression in a dose-dependent manner in the presence of 0.4 μg/mL lulizumab (i.e., the system drug, which is the final concentration of drug in the cell assay). In order to have the most sensitive NAb assay, the system drug level should be as low as possible while still having a good signal to noise ratio (S/N) and a low coefficient of variation (CV). As expected, the higher the drug concentration, the lower the signal of the luciferase reporter in the absence of the NAb PC (FIG. 2B & Table 9). Although system drug at 0.3 μg/mL had highest S/N for the whole NAb curve, attention should be payed to the lower end of NAb curve where the sensitivity of the NAb assay was dictated. Hence, 0.25 μg/mL system drug was chosen for further assay optimization; at this system drug level, NAb at 0.125, 0.25 and 0.5 g/mL consistently had higher S/N than the other two drug concentrations (Table 2).

TABLE 2

NAb curve with different concentration of drug. Only one of the three repeating experiments with similar results was shown here.

| NAb, | Raw Signal Drug, μg/mL | | | S/N Drug, μg/mL | | |
| --- | --- | --- | --- | --- | --- | --- |
| μg/mL | 0.3 | 0.25 | 0.2 | 0.3 | 0.25 | 0.2 |
| 8 | 21300 | 18335 | 17000 | 4.4 | 3.4 | 2.4 |
| 4 | 19430 | 17655 | 15530 | 4.0 | 3.3 | 2.2 |
| 2 | 17510 | 14765 | 15535 | 3.6 | 2.7 | 2.2 |
| 1 | 11010 | 11530 | 13705 | 2.3 | 2.1 | 2.0 |
| 0.5 | 8250 | 8870 | 11285 | 1.7 | 1.7 | 1.6 |
| 0.25 | 6610 | 7960 | 9130 | 1.4 | 1.5 | 1.3 |
| 0.125 | 6125 | 7265 | 7335 | 1.3 | 1.4 | 1.1 |
| 0 | 4865 | 5375 | 6980 | 1.0 | 1.0 | 1.0 |

3.3. Low Recovery of NAb in the Presence of Lulizumab with BEAD Treatment

Figure 3:
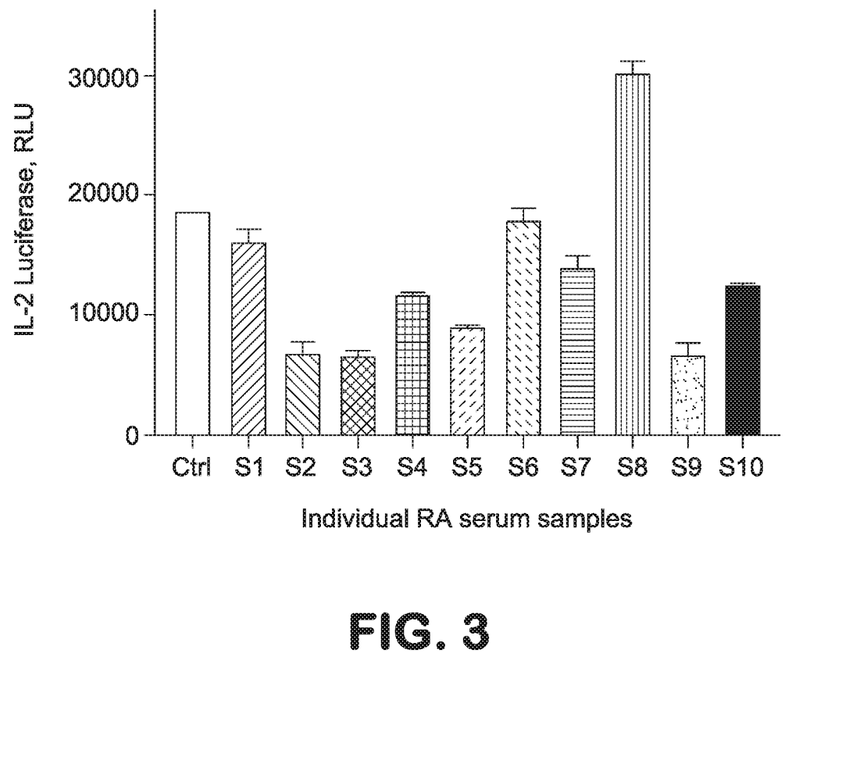
FIG. 3. Ten individual SLE sera were diluted 10 fold in assay medium and then added to a cell assay. Error bars stands for standard deviation from duplication wells.

Lulizumab is being developed for treatment of autoimmune and inflammatory diseases, where patients often express high amounts of inflammatory cytokines in circulation (14). As shown in FIG. 3, when ten individual systemic lupus erythematosus (SLE) sera were diluted 10-fold in assay medium and added to the cell-based assay, one sample (S8) had more than a 50% increase, and four samples (S2, S3, S5 & S9) had more than a 50% inhibition in luciferase raw signal when compared to the medium only control sample. This suggests that a 10-fold dilution is not enough to dilute out all interfering factors in SLE serum. However, fur dilutions result in reduced sensitivity of the NAb assay, since NAb in the samples will also be diluted out. For example, if the assay needs a 20-fold dilution and if the assay can only detect 0.5 μg/mL NAb after dilution, then the sensitivity of the NAb assay could potentially be as high as 10 μg/mL in the pure testing serum. The expected lulizumab level in the clinical samples is as high as 5 μg/mL, which means NAb below 15 μg/mL may not be detected if the samples were to be diluted and added to the assay without any extraction (the molecular weight of lulizumab is about 50-KDa and 15 μg/mL of NAb will all form immune complex with 5 μg/mL of lulizumab in a 1:1 molar ratio and will not be able to bind the system drug in the assay). Bead extraction with Acid Dissociation (BEAD) was first tested to see whether NAb PC could be dissociated from the drug in the sample with acid treatment, followed by binding to biotinylated-drug/bead complex, and being eluted from streptavidin-coated magnetic beads. This extraction will not only get rid of excessive amounts of drug in the samples, but also matrix factors that could interfere with the assay. Although BEAD has been successfully applied to multiple cell-based functional NAb assays, NAb activity after BEAD treatment was poor for the lulizumab NAb assay. If we set arbitrary cut point at relative NAb activity at 1.3, then the sensitivity of the NAb detection in the presence of 5 μg/mL of drug would be around 8 μg/mL (Tab. 2 and data not shown). No improvement was achieved after confirming that clone 13H4 was acid-stable and optimization of every critical step of extraction, such as increased amount of biotin-drug, increased amount of streptavidin-magnetic beads, as well as variant length of acid treatment at varied pH (data not shown). Although lulizumab has a small 12-kDa protein backbone, it has a 40-kDa branched PEG moiety, which occupies a huge space equal to that of a 500-kDa protein. It was hypothesized that under low pH, the branched PEG moiety may prevent (e.g., through steric hindrance) the interaction of NAb and biotinylated lulizumab protein, ultimately resulting in a low recovery of the NAb.

3.4. Thermal Stability of Lulizumab and Positive Controls

Figure 4:
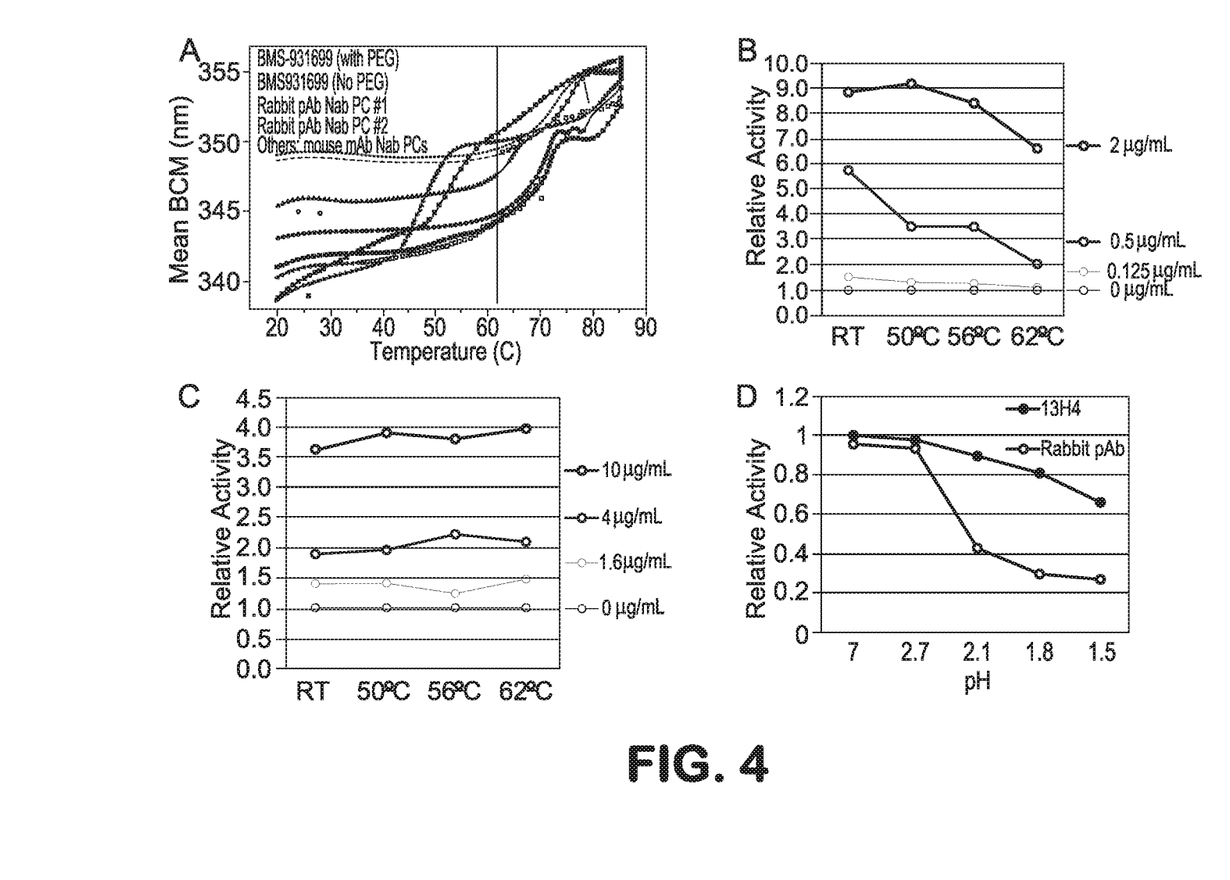
FIG. 4. Thermal stability of lulizumab and anti-lulizumab NAb PCs. A). Differential scanning fluorimetry (DSF) measured on UNcle platform to compare melting temperature of different proteins. Vertical orange bar indicates 62° C. B). Lulizumab; C). Anti-lulizumab NAb PC were heated at different temperature for 30 minutes, cooled down and then added to the cell-based assay. NAb activity was tested in the presence of 0.25 µg/mL drug. Raw value was normalized to 0 µg/mL group to show the relative activity. Only rabbit pAb is shown here, mAb clone 13H4 had similar results. D). pH stability of NAb PCs. Rabbit pAb or mouse mAb clone 13H4 NAb PCs were treated at different pH for 60 minutes, neutralized then added to cell assay. Raw value was normalized to pH 7.0 group to show the relative activity.

When compared to a 150-kDa NAb PCs, the unPEGylated lulizumab is very small at only 12-kDa. This prompted us to examine whether lulizumab may be selectively and irreversibly denatured upon heating, leaving behind intact NAb to be extracted by biotinylated unPEGylated drug. First, we compared the thermal stability of either PEGylated or unPEGylated lulizumab as well as a panel of anti-lulizumab NAb PCs prepared in PBS using differential scanning fluorimetry (DSF) on an UNcle platform. As shown in FIG. 4A & Table 3, lulizumab with or without PEG moiety had a much lower melting temperature so that most of them were already denatured at 62° C., while all NAb PCs including both pAb and mAb were just starting to denature under this temperature.

TABLE 3

Mean melting temperature of lulizumab and different NAb PCs measured by DSF.

| Sample ID | Mean $T_m$ (° C. ± SD) |
|---|---|
| PEG-lulizumab | 54.07 (0.06) |
| No PEG-lulizumab | 47.8 (0.1) |
| Rabbit pAb NAb PC1 | 72.0 (0.15) |
| Rabbit pAb NAb PC2 | 73.0 (0.1) |
| Mouse mAb PC1 | 72.9 (0.23) |
| Mouse mAb PC2 | 74.3 (0.3) |
| Mouse mAb PC3 | 64.9 (0.23) |
| Mouse mAb PC4 | 69.8 (0.11) |

To further confirm the different thermal stability of lulizumab and NAb PCs, Rabbit pAb #1 and clone 13H4 were heated at different temperature for 50-60 minutes and then added to the cell-based assay to test the remaining activity. While significant activity was lost for drug heated under 62° C., especially when drug concentration was low (around 0.5 µg/mL or less), all NAb PCs tested preserved their activity under all temperatures tested (FIG. 4B & 4C). These results suggested that under 62° C., most of the drug was irreversibly denatured while all NAb PCs tested remained active. Interestingly, when pH stability was tested for NAb PCs, mouse mAb clone 13H4 showed resistance to pH 2.1, the same pH used for the first acid treatment in BEAD, while rabbit pAb lost almost 60% of activity after pH 2.1 treatment (FIG. 4D). Similar poor pH stability was observed for polyclonal NAb PCs in other projects (data not show). The fact that the same rabbit pAb preserved almost all activity when heated at 62° C. suggested that heating could be a potential alternative for pH sensitive ADA/NAb dissociation.

3.5. Heating Instead of Acid-Treatment Increased Anti-Lulizumab NAb Recovery

With the promising thermal stability data showing significant difference between drug and NAb PCs, heating at 62° C. was evaluated as a substitute of the ineffectual first step of acid dissociation in BEAD extraction. Rabbit pAb or mouse mAb clone 13H4 at different concentrations in serum were incubated with or without 5 g/mL lulizumab for at least 4 hours at RT to ensure the formation of immune complex. Samples were then incubated in a pre-heated 62° C. heat-block, covered for 30 minutes; or treated with 400 mM Glycine, pH 2.0 for 60 minutes. Twenty-eight µL of the biotinylated-protein backbone of lulizumab (50 µg/mL), prepared either in PBS with 1% BSA or 1.8 M Tris, pH 8.8, were then added to a cooled plate or acid treated plate, respectively. After overnight incubation at 4° C., streptavidin-coated magnetic beads were added to pull down biotin-drug/NAb complexes. After bead wash, NAb was acid-eluted from the beads, neutralized, and finally added to the cell-based assay. As shown in Table 4, heating to dissociate drug/NAb immune complex had a much better NAb recovery than acid dissociation, we call this new procedure as Bead Extraction and Heating Dissociation (BEHD). For rabbit pAb PC, heating achieved relative NAb activity>1.5 at 4 µg/mL NAb, in both with or without drug group; while in the acid treatment group, only NAb at 16 µg/mL achieved relative NAb activity>1.5. Similarly, clone 13H4 at 4 µg/mL achieved relative NAb activity>1.6 when treated with heating while the same level of >1.6 relative NAb activity only occurred at 8-16 µg/mL in the acid treated group.

TABLE 4

Relative NAb activities after heating and acid treatment. Heating is better than acid to dissociate drug/NAb complex in the case of lulizumab. Raw values were normalized to 0 µg/mL NAb group to calculate the relative NAb activity.

| | | Acid | | Heating at 62° C. | |
|---|---|---|---|---|---|
| | | Rabbit pAb | 13H4 | Rabbit pAb | 13H4 |
| NAb only, µg/mL | 16 | 1.55 | 1.65 | 2.15 | 2.59 |
| | 8 | 1.43 | 1.60 | 1.71 | 2.26 |
| | 4 | 1.30 | 1.32 | 1.53 | 1.83 |
| | 0 | 1.00 | 1.00 | 1.00 | 1.00 |
| NAb + 5 µg/mL drug | 16 | 1.56 | 1.69 | 2.07 | 2.42 |
| | 8 | 1.34 | 1.55 | 1.58 | 1.85 |
| | 4 | 1.04 | 1.28 | 1.50 | 1.63 |
| | 0 | 1.00 | 1.00 | 1.00 | 1.00 |

3.6. Assay Validation

With the optimized cell assay and BEHD extraction, the assay was validated with the following parameters: cut point, precision, sensitivity, drug interference, selectivity and stability.

3.6.1 Cut Point

The cut point was assessed using 50 in-study, treatment-naive SLE patient serum samples. Each sample was run in duplicate over 2 plates by 3 analysts over 2 days. In addition to the SLE patient samples, each plate contained control samples. Positive control clone 13H4 (PCs) were prepared by spiking anti-lulizumab NAb into pooled serum from healthy donors. LPC was the low positive control neutralizing antibody at 3 µg/mL (LPC-1) or 2.5 µg/mL (LPC-2) in serum. Since the method has a pre-treatment of BEHD extraction, LPC-1 and LPC-2 was also prepared in the presence of 5 µg/mL lulizumab as LPC-extraction control (LPC-EXC), to monitor the BEHD extraction in each run. HPC was the high positive control neutralizing antibody at 10 µg/mL. NegC is the same pooled serum from healthy donors without PC. The PCs and NegC samples were run as 2 and 3 sets of duplicates on each plate, respectively. The acceptance criteria for each plate was set as the coefficient of variation, CV (%) of each PC≤30.0%. In addition, the average raw relative luminescence unit (RLU) value of NegC must be below that of LPC, LPC-EXC, and HPC. At least 4 of the 6 PCs (HPC, LPC and LPC-EXC) and at least one at each level must meet plate acceptance. At least 2 of the 3 NegC duplicates must meet % CV criteria.

The NegC was processed the same as the controls and patient samples. To account for possible fluctuations in RLUs across plates, the cut point for the SLE patient samples was calculated using the ratio of the sample RLU to the plate NegC RLU (ratio=RLU/NegC RLU). A strong correlation between SLE sample RLUs versus NegC RLUs across plates was observed (Pearson 'r'=0.96), supporting use of the NegC RLUs to correct for fluctuations in RLUs from plate to plate.

The normality assumption was confirmed by the Shapiro-Wilk test. After removal of outliers, the NAb assay cut point based on the ratio of Sample RLU/NegC RLU was determined to be 1.61 (99% confidence level, Table 5). Samples that yield a mean RLU/NegC RLU value≥1.61 are considered to be neutralizing.

TABLE 5

Determination of Neutralizing Assay Cut Point for the Systemic Lupus Erythematosus (SLE) Subject Samples.

| RLU/NegC RLU | All Samples n = 300 | Excluding Outliers n = 288[a] |
|---|---|---|
| Mean | 1.15 | 1.10 |
| Minimum, Maximum | 0.51, 3.04 | 0.64, 1.60 |
| Precision[b] (% CV): | | |
| Inter-Analyst: | 4.2 | 1.9 |
| Inter-Day: | 0.0 | 3.4 |
| Inter-Plate: | 8.6 | 6.5 |
| Inter-Subject: | 18.7 | 8.2 |
| Intra-Plate: | 17.3 | 12.3 |
| Cut Point Determination[c] | | |
| 1%: Mean + 2.33*TotalSD | | 1.61 |

[a]Statistical outliers (nominal n = 6):
[b]Precision estimates of 0.00% indicate that variation was greater among and/or within plates and subjects than between days and/or analysts and an estimate could not be calculated.
[c]Log-transformed data used

3.6.2 Precision

Precision assessments (CV [%]) were performed across all 12 runs for the PC ratios (PC/NegC RLU ratios). See Table 6. Analyses were performed separately for each control sample and the donor samples as described in Section 2.7.1. All precision estimates, including total precision, were within 18.4% (% CV) across all control samples. Since only HPC/NegC had a lower bound on one-sided 99% prediction interval higher than cut point of 1.61, the acceptance criteria for HPC/NegC is ≥1.94 while all other PCs are ≥cup point of 1.61.

TABLE 6

Precision Assessment and Summary of the Assay PC/NegC RLU Ratios

| RLU/NegC Ratios | LPC-1/ NegC n = 24 | LPC-2/ NegC n = 24 | LPC-Exc-1/ NegC n = 24 | LPC-Exc-2/ NegC n = 24 | HPC/ NegC n = 24 |
|---|---|---|---|---|---|
| Mean | 2.32 | 2.09 | 2.08 | 1.73 | 2.92 |
| Minimum, Maximum | 1.76, 2.96 | 1.47, 2.66 | 1.48, 2.78 | 1.06, 2.26 | 2.25, 3.93 |
| Precision[a] (% CV): | | | | | |
| Inter-Analyst: | 0.0 | 2.1 | 6.5 | 3.8 | 0.0 |
| Inter-Day: | 3.6 | 0.0 | 0.0 | 0.0 | 0.0 |
| Inter-Plate: | 0.0 | 0.0 | 0.0 | 0.0 | 4.1 |
| Intra-Plate: | 15.0 | 14.7 | 16.1 | 18.0 | 14.3 |
| Total | 15.4 | 14.8 | 17.4 | 18.4 | 14.9 |
| Lower Bound on One-Sided 99% Prediction Interval[b]: | 1.49 | 1.37 | 1.28 | 1.01 | 1.94 |

[a]Precision estimates of 0.0% indicate that variation was greater among and/or within plates than between days and/or analysts and an estimate could not be calculated. Average of plate duplicates was used.
[b]Log-transformed data used for prediction interval calculation.

3.6.3 Selectivity

Selectivity was assessed with 20 individual SLE human serum study samples. The samples were run unspiked and spiked at the LPC level of anti-lulizumab (3 µg/mL). Seventy five percent of the unspiked samples were negative and 100% of the samples spiked at LPC were positive (Table 7).

TABLE 7

Selectivity assessment in SLE serum.

| | RLU/NegC | |
|---|---|---|
| Individual No. | Blank serum | LPC (3 µg/mL) |
| 1 | 1.46 | 3.06 |
| 2 | 1.43 | 2.98 |
| 3 | 1.75 | 3.34 |
| 4 | 1.27 | 3.01 |
| 5 | 1.38 | 2.98 |
| 6 | 1.48 | 2.57 |
| 7 | 1.39 | 3.25 |
| 8 | 1.97 | 3.00 |
| 9 | 1.65 | 2.71 |
| 10 | 1.59 | 3.07 |
| 11 | 1.45 | 2.38 |
| 12 | 1.19 | 2.08 |
| 13 | 1.05 | 2.68 |
| 14 | 1.20 | 3.14 |
| 15 | 1.29 | 2.85 |
| 16 | 1.53 | 3.20 |
| 17 | 1.53 | 2.99 |
| 18 | 1.78 | 2.98 |
| 19 | 1.51 | 2.44 |
| 20 | 1.78 | 2.56 |

3.6.4 Sensitivity

Figure 5:
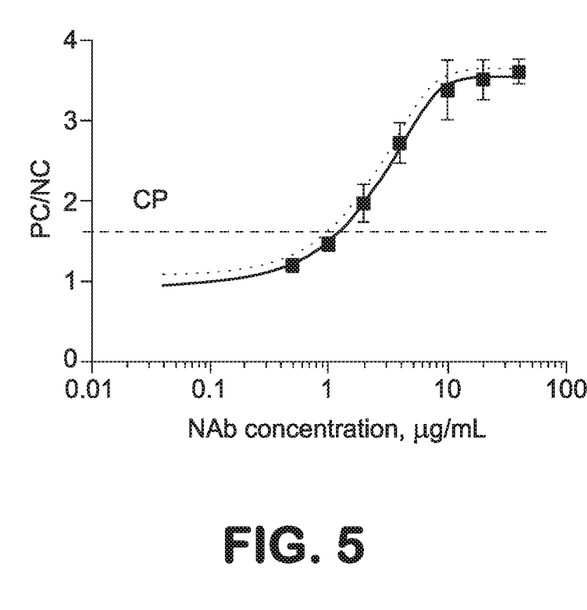
FIG. 5. Determination of assay sensitivity. NAb PC was spiked into pooled normal human serum, BEHD extracted and run in the cell-based assay. Error bars indicate standard deviation from 6 sets of data.

Assay sensitivity is defined as the lowest concentration at which the affinity purified mouse anti-lulizumab NAb PC consistently produces a result at or above the cut point of 1.61. The PC antibody was spiked into pooled normal human serum at 40, 20, 10, 4, 2, 1 and 0.5 µg/mL. A total of 6 curves were run by 3 analysts over 2 days during the cut point evaluation. The lowest concentration of PC that was reliably tested as positive in all these runs was found to be at 2.0 µg/mL. All 6 curves were analyzed with four parameter logistic (4PL) function and interpolated at 1.61 using GraphPad Prisma software. The media value is 1.31 hence the estimated sensitivity of the assay is set as 1.31 µg/mL (FIG. 5).

3.6.5 Drug Interference

LPC-1 at 3 µg/mL and NegC were spiked with 10, 5, 2.5 and 1 µg/mL of lulizumab to estimate the drug tolerance of the assay. LPC spiked with lulizumab was able to produce a positive response at the highest concentration tested (10 µg/mL) and all NegC samples spiked with lulizumab produced a negative (non-neutralizing) result, hence the assay can tolerate higher than 10 µg/mL drug at LPC-1 level. (Table 8).

TABLE 8

Drug interference of the assay. NAb PC at LPC level (3 µg/mL) can be detected in the presence of 10 µg/mL drug in the samples.

| Concentration, µg/mL | | |
|---|---|---|
| NAb PC | Drug | RLU/NegC |
| 3 | 10 | 2.67 |
| 3 | 5 | 2.59 |
| 3 | 2 | 3.39 |
| 3 | 1 | 2.93 |
| 3 | 0 | 3.27 |
| 0 | 10 | 1.28 |
| 0 | 5 | 1.59 |
| 0 | 2 | 1.55 |
| 0 | 1 | 1.53 |
| 0 | 0 | 1.5 |

3.6.6 Stability of NAb PC

The room temperature and freeze-thaw stability of anti-lulizumab NAb PC in human serum was evaluated using HPC, LPC-1 and LPC-1-EXC levels. Three aliquots of each control level were subjected to ambient room temperature for 24 hours, or were subjected to 10 freeze-thaw cycles. The samples were assayed and classified relative to the cut point. All samples met the screening criteria at each condition which confirms that the NAb PC is stable for 24 hours at ambient room temperature, or up to 10 freeze-thaw cycles (Table 9).

TABLE 9

Stability testing. PCs were stable when left at room temperature for 24 hours or after 10 freeze-thaw cycles.

| | | PC/NegC ratio | |
|---|---|---|---|
| PC | Plate control | Room temperature | Freeze-thaw |
| HPC1 | 3.69 | 4.75 | 4.33 |
| HPC2 | 3.09 | 5.49 | 4.00 |
| HPC3 | — | 5.16 | 4.00 |
| LPC1 | 2.98 | 4.76 | 2.53 |
| LPC2 | 2.60 | 3.78 | 2.63 |
| LPC3 | — | 4.03 | 3.62 |
| LPC-EXC1 | 2.54 | 2.99 | 3.55 |
| LPC-EXC2 | 1.94 | 3.35 | 3.26 |
| LPC-EXC3 | — | 3.86 | 3.34 |

4. Discussion

One of the major challenges for a cell-based functional NAb assay, especially for mAb biotherapeutics, is the high amount of drug present in patient test samples, which often interferes with detection of NAb in the cell-based assays (16, 17).

In a typical ADA assay, biotin-conjugated drug and HRP- or Ruthenium-labeled drug is added to test samples to compete against circulating drug for ADA in the samples; as long as enough ADA can form a complex with labeled drugs, the samples will be tested as ADA positive in the bridging assay. In other words, in the presence of excess labeled drug, it is possible to shift the equilibrium to favor ADA-labeled drug complex formation over ADA-circulating drug complexes (18). In a cell-based NAb assay however, the cells cannot distinguish drug in the samples vs. the added drug such as biotinylated drug: all drug present can have direct or indirect impact on the cells. Hence, if drug levels exceed a 1:1 molar ratio to the NAb, NAb will not be detected unless the excess drug is removed before addition to the cell-based assay. The first successful method to remove high amounts of drug for immunogenicity testing is SPEAD, Solid Phase Extraction with Acid Dissociation: samples containing drug/ADA immune complex are first incubated with biotinylated drug overnight to form the biotin-drug/ADA complex; these complexes are then captured by a high-bind streptavidin-coated plate. After washing, ADA are eluted from the biotin-drug using acid (19). There are two limitations to this original SPEAD method: 1) some ADA/NAb PCs have high affinity with very low off rate, so that overnight incubation is not enough to form a new equilibrium in favor of biotin-drug/ADA complex. 2) In addition, high-bind plates have a limited binding capacity, which limits the amount of biotinylated drug to be added; if the drug in the test sample is too high, the limited amount of biotinylated drug added can only recover a small percentage of ADA/NAb, leading to low drug tolerance and low NAb detection. For these reasons, BEAD evolved from SPEAD. An acid dissociation step was added to replace the overnight incubation without acid, and streptavidin-coated magnetic beads with much more binding surface are used to replace the plate so that more biotin-drug can be added, resulting in a more efficient competition for ADA/NAb binding (10).

Although the BEAD method has been successfully applied to multiple NAb assays, we recently found that as high as 40% of a panel of 15 NAb PCs we tested are acid labile and not able to withstand the harsh acid treatment, resulting in low NAb recovery (data in preparation). This implies that at least some of the NAb species in the real test samples could also be acid sensitive and may not be detected after BEAD extraction.

In the current manuscript, we further demonstrate that new modalities of biotherapeutics, such as PEGylated domain Ab, may not be compatible with BEAD extraction. In the current case study, we took advantage of the low melting temperature of lulizumab, when compared to a full 150-kDa of NAb. The 62° C. heating step not only dissociates NAb/drug complex to replace the harsh acid treatment in BEAD, but it also irreversibly denatures the majority of the drug in the test samples, leaving behind the intact NAb to be extracted by an unPEGylated biotin-lulizumab. The irreversible denaturing of the drug is desired since a reduced amount of functional drug in the sample facilitates the equilibrium toward ADA/biotinylated drug complex, resulting in an increase yield of extracted ADA. Notably, a rabbit pAb NAb PC with poor low pH stability survived heating at 62° C., suggesting that heating could be a potential alternative for pH sensitive ADA/NAb dissociation.

We were able to validate the assay with good accuracy, precision and sensitivity. The same bead extraction with heating dissociation method, which we named BEHD, could be applied to any other biotherapeutics that have a sufficiently lower melting temperature than full human Abs. To our knowledge, this is the first report of using heat to facilitate the extraction of ADA/NAb in immunogenicity testing.

5. References

1. Schellekens H. Bioequivalence and the immunogenicity of biopharmaceuticals. Nat Rev Drug Discov. 2002; 1 (6): 457-62.
2. Scheinfeld N. A comprehensive review and evaluation of the side effects of the tumor necrosis factor alpha blockers etanercept, infliximab and adalimumab. J Dermatolog Treat. 2004; 15 (5): 280-94.
3. Casadevall N, Nataf J, Viron B, Kolta A, Kiladjian J J, Martin-Dupont P, et al. Pure red-cell aplasia and antierythropoietin antibodies in patients treated with recombinant erythropoietin. N Engl J Med. 2002; 346 (7): 469-75.
4. Kuus-Reichel K, Grauer L S, Karavodin L M, Knott C, Krusemeier M, Kay N E. Will immunogenicity limit the use, efficacy, and future development of therapeutic monoclonal antibodies? Clin Diagn Lab Immunol. 1994; 1 (4): 365-72.
5. Koren E, Zuckerman L A, Mire-Sluis A R. Immune responses to therapeutic proteins in humans—clinical significance, assessment and prediction. Curr Pharm Biotechnol. 2002; 3 (4): 349-60.
6. Schellekens H, Casadevall N. Immunogenicity of recombinant human proteins: causes and consequences. J Neurol. 2004; 251 Suppl 2: II4-9.
7. Food and Drug Administration. DRAFT-Guidance for Industry Immunogenicity Assessment for Therapeutic Protein Products. U.S. Department of Health and Human Services. 2013.
8. Hu J, Gupta S, Swanson S J, Zhuang Y. A bioactive drug quantitation based approach for the detection of anti-drug neutralizing antibodies in human serum. J Immunol Methods. 2009; 345 (1-2): 70-9.
9. Lofgren J A, Wala I, Koren E, Swanson S J, Jing S. Detection of neutralizing anti-therapeutic protein antibodies in serum or plasma samples containing high levels of the therapeutic protein. J Immunol Methods. 2006; 308 (1-2): 101-8.
10. Xu W, Jiang H, Titsch C, Haulenbeek J R, Pillutla R C, Aubry A F, et al. Development and characterization of a pre-treatment procedure to eliminate human monoclonal antibody therapeutic drug and matrix interference in cell-based functional neutralizing antibody assays. J Immunol Methods. 2015; 416:94-104.
11. Milliken G A J D. Analysis of Messy Data, Volume I: Designed Experiments. Wadsworth, Inc, CA. 1984:211-45.
12. Shankar G, Devanarayan V, Amaravadi L, Barrett Y C, Bowsher R, Finco-Kent D, et al. Recommendations for the validation of immunoassays used for detection of host antibodies against biotechnology products. J Pharm Biomed Anal. 2008; 48 (5): 1267-81.
13. Shi R, Honczarenko M, Zhang S, Fleener C, Mora J, Lee S K, et al. Pharmacokinetic, Pharmacodynamic, and Safety Profile of a Novel Anti-CD28 Domain Antibody Antagonist in Healthy Subjects. J Clin Pharmacol. 2017; 57 (2): 161-72.
14. Kuhn A, Landmann A, Wenzel J. Advances in the treatment of cutaneous lupus erythematosus. Lupus. 2016; 25 (8): 830-7.
15. Yang Z, Wang H, Salcedo T W, Suchard S J, Xie J H, Schneeweis L A, et al. Integrated Pharmacokinetic/Pharmacodynamic Analysis for Determining the Minimal Anticipated Biological Effect Level of a Novel Anti-CD28 Receptor Antagonist BMS-931699. J Pharmacol Exp Ther. 2015; 355 (3): 506-15.
16. Gupta S, Indelicato S R, Jethwa V, Kawabata T, Kelley M, Mire-Sluis A R, et al. Recommendations for the design, optimization, and qualification of cell-based assays used for the detection of neutralizing antibody responses elicited to biological therapeutics. J Immunol Methods. 2007; 321 (1-2): 1-18.
17. Gupta S, Devanarayan V, Finco D, Gunn G R, 3rd, Kirshner S, Richards S, et al. Recommendations for the validation of cell-based assays used for the detection of neutralizing antibody immune responses elicited against biological therapeutics. J Pharm Biomed Anal. 2011; 55 (5): 878-88.
18. Mire-Sluis A R, Barrett Y C, Devanarayan V, Koren E, Liu H, Maia M, et al. Recommendations for the design and optimization of immunoassays used in the detection of host antibodies against biotechnology products. J Immunol Methods. 2004; 289 (1-2): 1-16.
19. Smith H W, Butterfield A, Sun D. Detection of antibodies against therapeutic proteins in the presence of residual therapeutic protein using a solid-phase extraction with acid dissociation (SPEAD) sample treatment prior to ELISA. Regul Toxicol Pharmacol. 2007; 49 (3): 230-7.

EQUIVALENTS

Those skilled in the art will recognize or be able to ascertain, using no more than routine experimentation, many equivalents of the specific embodiments of the invention described herein. Such equivalents are intended to be encompassed by the following claims.

We claim:

1. A method for detecting an anti-drug antibody (ADA) in an ADA: drug immune complex sample, comprising:
   a) pre-treating the sample at a high temperature between 60° C. and 68° C. to dissociate the ADA: drug immune complex in the sample and selectively denature the drug;
   b) isolating the dissociated ADA from the sample by a matrix;
   c) retrieving the dissociated ADA from the matrix using a buffer; and
   d) detecting the dissociated ADA in a cell-based assay or an in vitro assay,
   wherein the drug is selected from the group consisting of an antibody or fragment thereof, a nucleic acid, a peptide, a polypeptide, a peptidomimetic, a carbohydrate, a lipid, or a small molecule compound, and
   wherein the drug has a lower thermal stability than the ADA and wherein the ADA is sensitive to acid treatment.

2. The method of claim 1, wherein the high temperature is at about 60° C., 61° C., 62° C., 63° C., 64° C., 65° C., 66° C., 67° C. or 68° C.

3. The method of claim 1, wherein the sample is pre-treated at the high temperature for a period between about 30 minutes and 2 hours.

4. The method of claim 1, wherein the sample is a biological sample selected from the group consisting of mucus secretion, saliva, blood, whole blood, plasma, and serum.

5. The method of claim 1, wherein the ADA is isolated from the sample by contacting with a biotinylated drug, followed by a streptavidin-coated matrix.

6. The method of claim 1, wherein the ADA is isolated from the sample by a matrix coupled with the drug.

7. The method of claim 6, wherein the matrix is a magnetic bead.

8. The method of claim 1, wherein the retrieved ADA is detected in a cell-based assay.

9. The method of claim 8, comprising: i) adding the retrieved ADA to a cell in the presence of the drug; and ii) detecting the ADA by measuring the reduction of activity of the drug on the cell.

10. The method of claim 1, wherein the retrieved ADA is detected in an in vitro assay.

11. The method of claim 10, comprising: i) contacting the retrieved ADA with the drug labeled with a detectable label; and ii) detecting the ADA by measuring the detectable label.

12. The method of claim 1, wherein the drug is a domain antibody.

13. The method of claim 1, wherein the drug is pegylated.

14. The method of claim 1, wherein the high temperature is at about 62° C.

15. The method of claim 1, wherein the sample is serum.

16. The method of claim 1, wherein the sample is from a subject which has been treated with the drug.

\* \* \* \* \*